United States Patent [19]

Edsall et al.

[11] Patent Number: 5,733,151
[45] Date of Patent: Mar. 31, 1998

[54] ELECTRICAL CLAMPING CONNECTION DEVICE

[76] Inventors: David Edsall, 2572 Evans Ave., Louisville, Colo. 80027; Scott Miller, 1341 Tipperary St., Boulder, Colo. 80303; Steve Stracener, P.O. Box 731, 224 Walnut Dr., Frederick, Colo. 80530

[21] Appl. No.: 702,350

[22] Filed: Aug. 23, 1996

[51] Int. Cl.⁶ .................................................. H01R 4/48
[52] U.S. Cl. ............................. 439/729; 439/67; 439/909
[58] Field of Search ............................... 439/493, 909, 439/67, 729

[56] References Cited

U.S. PATENT DOCUMENTS

| | | | |
|---|---|---|---|
| 4,121,575 | 10/1978 | Mills et al. | 128/2.06 E |
| 4,353,372 | 10/1982 | Aver | 128/640 |
| 4,702,256 | 10/1987 | Robinson et al. | 439/909 |
| 4,763,660 | 8/1988 | Kroll et al. | 128/640 |
| 5,184,620 | 2/1993 | Cudahy et al. | 128/639 |
| 5,387,122 | 2/1995 | Goldberger et al. | 439/909 |
| 5,419,337 | 5/1995 | Dempsey et al. | 128/702 |
| 5,454,739 | 10/1995 | Strand | 439/729 |

FOREIGN PATENT DOCUMENTS

| | | | |
|---|---|---|---|
| 0 275 811 A1 | 7/1988 | European Pat. Off. | A61B 5/04 |
| 3637956 A1 | 6/1987 | Germany | A61N 1/04 |
| 2185403 | 7/1987 | United Kingdom | A61N 1/04 |
| WO 90/01898 | 3/1990 | WIPO | A61B 5/04 |
| WO 92/07509 | 5/1992 | WIPO | A61B 5/044 |
| WO 96/14015 | 5/1996 | WIPO | A61B 5/0408 |

*Primary Examiner*—Neil Abrams
*Assistant Examiner*—T. C. Patel
*Attorney, Agent, or Firm*—Mintz, Levin, Cohn, Ferris, Glovsky and Popeo, P.C.

[57] ABSTRACT

An electrical connection clamping device for use with a flexible medical electrode harness comprises an upper member and a housing member. The housing member has a first surface with at least one electrical contact point, alignment and bias devices. The upper member has a first end with clamping device and a second end pivotally connected to the bias device of the housing member. The alignment device receive a flexible medical circuit and allow the electric contact points to electrically connect with the circuit as it is secured by the clamping device. A cable is electrically connected to the electrical contact points and to an instrument. The cable has a plurality of individually sheathed wire bundles which each have a plurality of individual wires for attachment to a printed circuit board and electrical contact points.

9 Claims, 5 Drawing Sheets

ELECTRICAL CLAMPING CONNECTION DEVICE

FIELD OF THE INVENTION

This invention relates to a device for connecting and securing electrical circuits, and more particularly to a device which electrically connects medical sensors and monitors to instrumentation devices.

BACKGROUND OF THE INVENTION

In the health care industry, electrical measurement instrumentation connects and disconnects to many different types of circuits every day, especially in an emergency care situation. A large majority of these circuits are from devices known as flexible circuits which are used in picking up electrical signals associated with various biological functions of patients. The flexible circuit or "flex circuit" is basically a circuit formed on a mechanically flexible substrate material. Flexibility is desired in the implementation and design to conform with the human torso and various locations and positions on the human body where circuitry may be needed in a given situation. These flexible circuits are designed for use on a single patient and typically are not reusable. These flexible circuits must be connected to some type of electrical connector to allow the instrumentation to read the electrical signals from the patient. However, most commercially available connectors for flexible circuits are designed for use inside an instrument case, which allows connection of the flexible circuit to a liquid crystal display in a portable personal computer or the like, and are designed only for five to ten connect/disconnect cycles. This is by no means cost efficient, as more than 2,500 connect/disconnect cycles are typically required in a one year period.

A low cost and convenient connection system is therefore desired to allow medical personnel to attach measurement instrumentation to the flexible circuit. The connection system should be capable of surviving the in-use environment over a large number of connect/disconnect cycles and for a long period of time, perhaps in excess of one year. Since these connectors are often used in emergency situations, the cable and connector system should preferably provide low noise, high quality signals, low interconnection impedance for quality results and in addition be fast and easy to use by medical personnel. It should also be kept in mind that as medical personnel would be using this in emergency situations, the device should ideally be operable with minimal effort, including the possibility of using only one hand to operate the device when the other hand is occupied with emergency equipment.

An additional problem in medical instrumentation is in the area of cables and shielding for these cables. Previous implementations of cabling for medical instrumentation, such as multi-conductor ECG patient cable, have utilized shielding where appropriate to reduce external noise, such as the 50 or 60 Hz mains noise from the AC power net. In cables which require a large number of conductors, the conductors are typically individually shielded and loose packed in a sheath to provide both shielding and flexibility. Miniature coaxial cable is very expensive (approximately $100 per foot for an 85 conductor cable), and terminating it is time consuming since each shield must be individually stripped of insulation and the braid of cable stripped back until finally the center conductor is stripped and terminated.

Attempts at bundling all of the wires together into a single bundle which is then shielded as a whole have failed, since the shielding binds the bundle together so tightly that the cables cannot slip over each other and as a result the cable is very inflexible and unbendable. This can make a difference in emergency situations of the medical industry where the flexibility of the cable may be required in order to move electric connectors and devices into proper position for patient care on a split second notice. Additionally, it is desired to avoid a stiff cable from peeling a sensor off of a patient. Therefore, an improved cable and shielding system is desired to provide improved flexibility, signal integrity, and cost efficiency.

Similar problems have been experienced outside of the medical industry, and it would therefore be desirable for an improved system anywhere a flexible electric circuit may be used.

SUMMARY OF THE INVENTION

The present invention overcomes the disadvantage of the prior art devices by providing an electrical clamping and connection device for use in transmitting electrical signals associated with various biological functions of patients from the electrode to the medical instrumentation device. Additionally, the present invention can be utilized anywhere that a flexible electric circuit may be used, including but not limited to electronic applications for commercial products. The electrical clamping and connection device of the present invention provides a housing member having a first surface and an upper member. Each of these members has first and second ends. The housing member has at least one electrical contact point, an alignment device and a bias device located on the first surface. The alignment device and electrical contact point are positioned preferably near the first end with the bias device preferably positioned at the opposite end. The upper member has a clamping device and the second end is pivotally connected to the bias device of the housing member. In this manner, the alignment device of the housing member is positioned to receive an electrical circuit which has conductive pads. These pads electrically connect to the electric contact points of the housing member with proper and sufficient electrical contact ensured by the clamping device of the upper member holding the electric circuit contact pads in alignment with the electric contact points of the housing member.

The electric signals received from the electric circuit are transmitted through the electric contact points to a printed circuit board which is in electric communication with a cable system to thereby provide the electric signal to the medical instrumentation device.

The cable system in the present embodiment uses groups of wires which are bundled together and are shielded as subcables or groups. Each group has an intermediate sheath to allow relative movement between groups. The groups are then loosely packed in the outer sheath to allow flexibility within the outer sheath, and therefore greater flexibility of the entire cable.

BRIEF DESCRIPTION OF THE INVENTION

DETAILED DESCRIPTION

Figure 1:
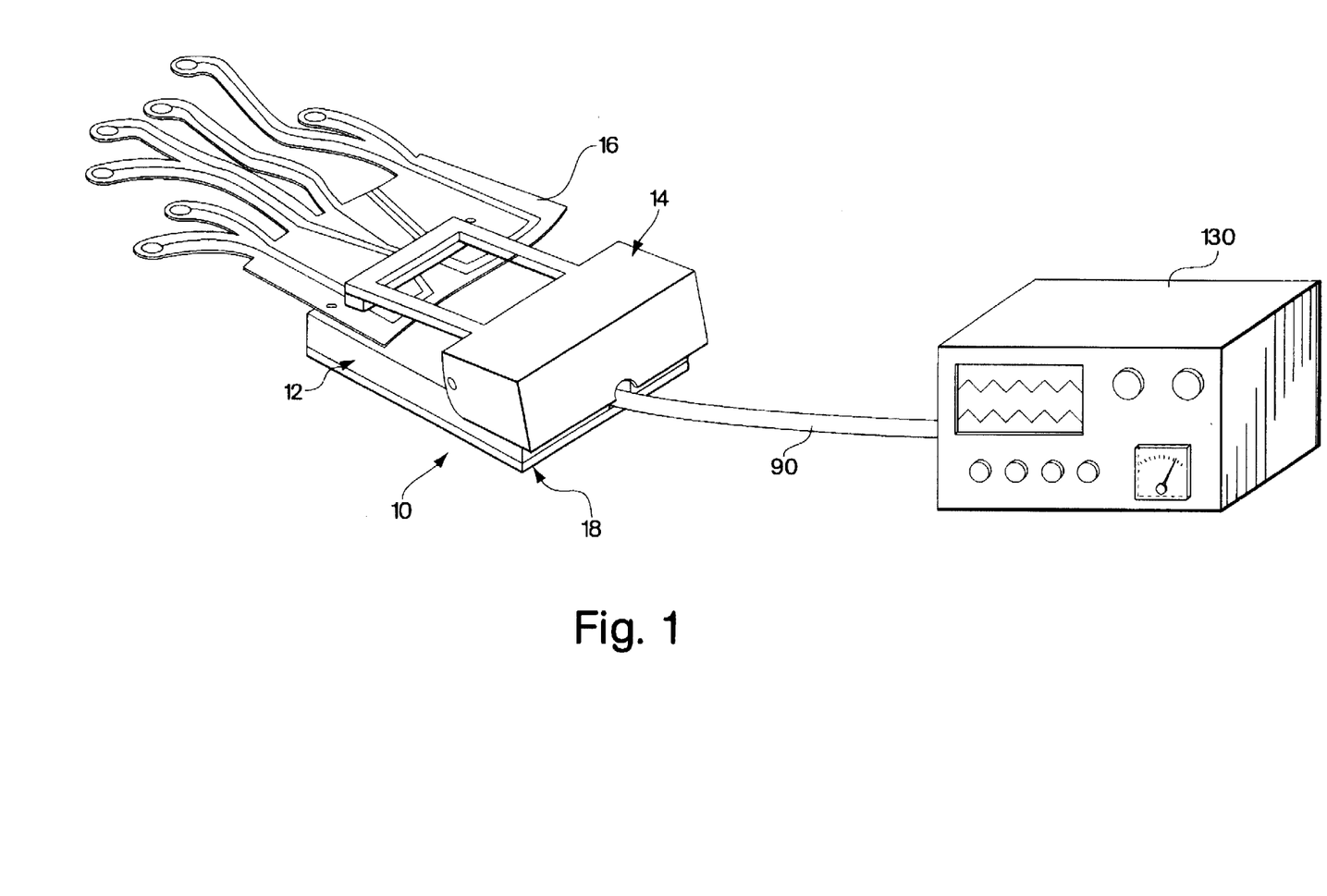
FIG. 1 is a partial perspective view of the electrical connection and clamping device of the present invention.

Referring now to FIG. 1, there is shown one embodiment of the device 10 of the present invention. The electrical clamping connection device 10 comprises a housing member 12, an upper member 14 and a base 18. A flexible electrical circuit 16 is positioned on the device 10 and electrical signals associated with various biological functions of humans are electrically transmitted to proper medical instrumentation.

Figure 2:
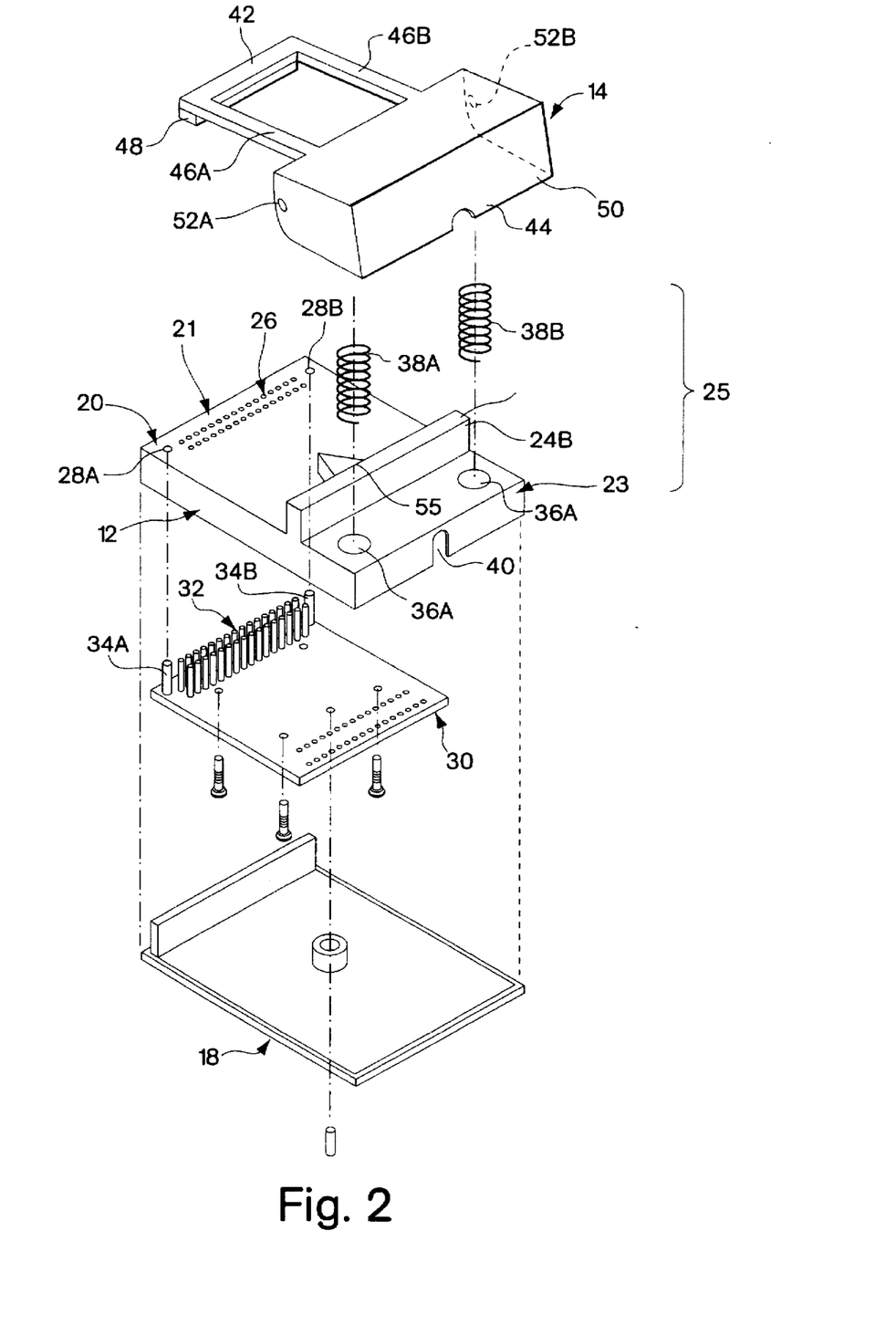
FIG. 2 is an exploded perspective view of the electrical connector and clamping device of the present invention.

Referring now to FIGS. 1 and 2, a more detailed description and understanding of the device 10 can be made. The housing member 12 has a first surface 20 with first and second ends 21 and 23, respectively. Positioned at the first end 21 of the housing member 12 is at least one electrical contact point and an alignment device for the flexible circuit. The electrical contact point may include at least one, but preferably a multitude of electrically conductive contact pins 32 or other similar electric contact points. These electrical contact pins 32 may be formed on the first surface 20 of the housing member 12, or protrude through a plurality of contact holes 26 which are located at the first end 21 of the first surface 20 of the housing member 12. In this embodiment, the contact pins 32 would be positioned on a printed circuit board 30 which is positioned beneath and encased by the housing member 12, with the base plate 18 securing the printed circuit board 30 in a fixed relation with the housing member 12. The electrically conductive contact pins may be made of or plated with any electrically conductive material, such as gold, silver, copper, etc.

Similarly, the alignment means may comprise at least one alignment pin 34 which may be integrally formed on the first surface of the housing member 12, or protrude through the first surface 20 through alignment holes 28A and 28B. In this embodiment, the alignment means could comprise pins 34A and 34B located on the printed circuit board 30. These alignment pins would protrude through the housing member at the alignment holes 28A and 28B.

The housing member 12 has a second end 23 with bias device 25. The bias device 25 can comprise a pivot bar 22, a pivot axis located along the pivot bar 22, and includes pivot points 24A and 24B. The housing member and pivot bar may be integrally formed from a single nonconductive material. The housing member can be produced by various molding machining, or casting techniques which are well known in the art, but no limitation is intended. The bias device may also include a spring system such as springs 38A and 38B positioned at the second end 23 of the housing member 12. Other bias devices can include slots, levers, electric buttons, switches. Other such bias devices are known to those skilled in the art and are intended to be within the scope of the present invention.

The housing member 12 may further include a conduit opening 40 for receiving a wire or cable 90 from the medical instrumentation device 130. The cable 90 (FIG. 3) would receive the electrical signals from the printed circuit board 30 and the contact points 32 and transfer the signal to the medical instrument.

The upper member 14 includes a first end 42, a second end 44 and at least one arm 46 connecting the first and second ends 42 and 44. The first end 42 has clamping device 48, and the second end 44 includes a cover piece 50.

The upper member 14 connects and cooperates with the bias device 25 of the housing member 12 to allow the upper member 14 to be lifted by the user, preferably with one hand, and returned to its original position by the bias means or device 25. This can be accomplished by a pair of pivot receiving points 52A and 52B of the upper member 14 which pivotally engage the pivot points 24A and 24B respectively of the housing member 12. The cover piece 50 would then be positioned over the coil or torsion springs 38A and 38B, and thereby compress the springs 38A and 38B when the first end 42 of the upper member 14 is lifted to a raised or second position and the bias device 25 would return the upper member 14 to the initial lower position by rotating or pivoting the upper member 14 along pivot points 24A and 24B of the housing member 12.

The first end 42 of the upper member 14 has a clamping apparatus 48 located at the underside of the upper member 14. This clamping apparatus 48 is fastened to the first end 42 by conventional methods, including but not limited to adhesives, and may comprise a nonconductive pad, such as rubber or other elastomers, but no limitation is intended. Various shapes and sizes of pads can be used. The clamping device 48 will be in contact with the upper side of the flexible electric circuit 16 when the circuit 16 is positioned on the alignment device and the electrical contact 32 of the housing member 12. The upper member can be formed from similar manufacturing methods of the housing member 12 and can be made of any nonconductive material.

In assembly, the electrical connection clamping device 10 of the present invention has the housing member 12 and upper member 14 pivotally connected along pivot bar 22 at pivot points 24A and 24B. The cover piece 50 of the upper member 14 would enclose and contact the bias device 25, including any possible springs 38A and 38B. The positioning of the pivot bar 22 with pivot points 24A and 24B would be such that they cooperate with pivot receiving points 52A and 52B of the upper member 14 to allow the clamp 48 of the upper member 14 to align above the electrical contact points 32. This feature will also determine the proper length of the arm area 46 to align the clamping means 48 above the electrical contact points.

The housing member 12 may cover a printed circuit board 30 and a base member 18. The printed circuit board 30 is made of a nonconductive material such as fiberglass or plastic and may include the alignment apparatus 34, such as pins or clips or other known methods in the art, and the electric contact points 32. The printed circuit board 30 would be capable of receiving electric signals from the flexible circuit 16 and transferring them to the medical instrumentation via a cable or wire (See FIG. 3). The primed circuit board 30 may be secured in position by a fastener on the base member 18 and may also provide fasteners to secure the printed circuit board 30 in relation to the housing member 12. Additionally, fasteners may be provided on the printed circuit board 30 to protrude through the first surface 20 of the housing member 12 to secure additional items. The base member 18 can be fastened to the housing member 12 by any known means in the art such as screws, clips or even snap on methods, but no limitation is intended.

Figure 3:
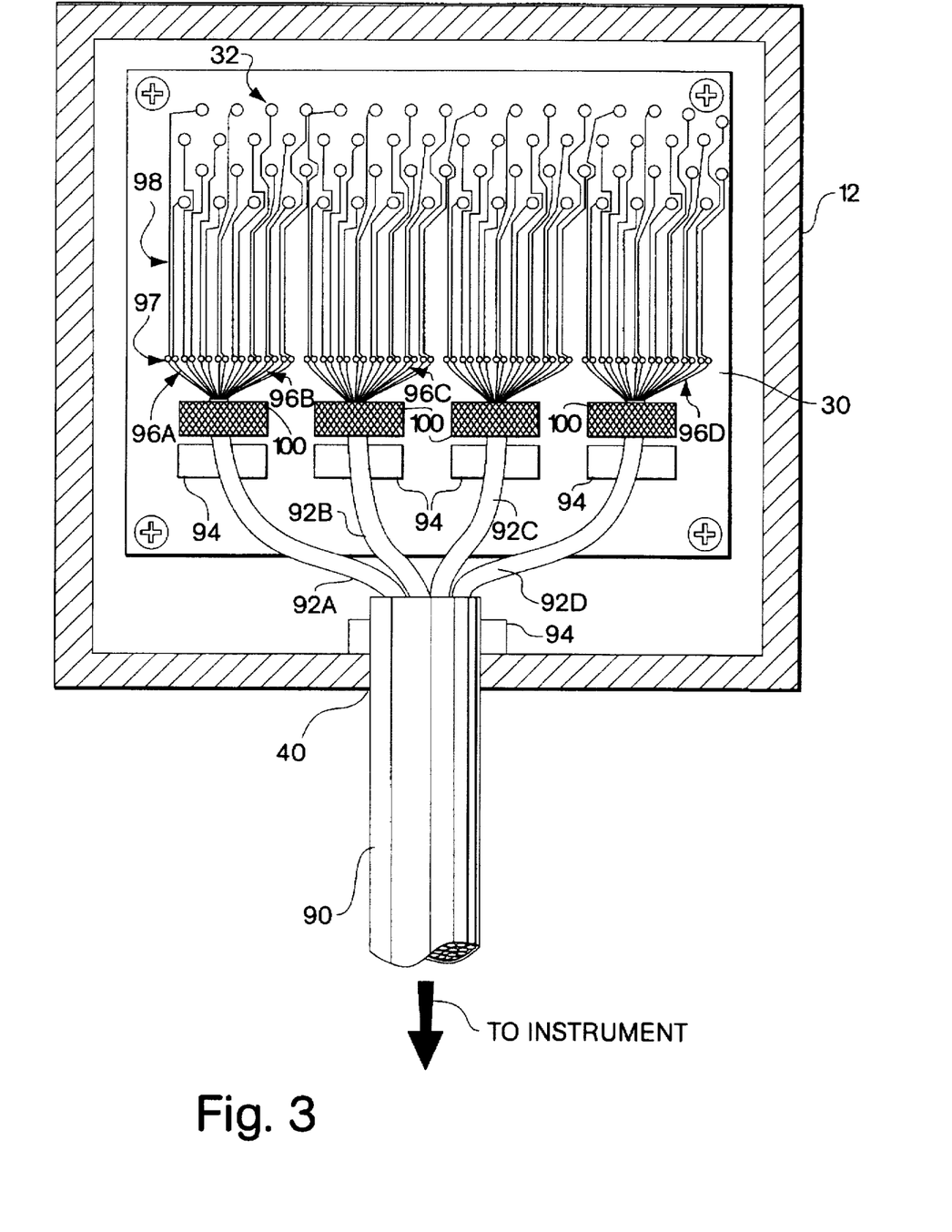
FIG. 3 is a top view of the cable connection on the printed circuit board.

The upper member 14, housing member 12 and base 18 are all preferably made from nonconductive materials and may be made by molding methods known in the art, but no limitation is intended. While one particular method of forming these items has been disclosed herein, it is to be understood that the method of forming the items is not limiting and that other appropriate methods of forming will be apparent to those skilled in the art. Such methods are intended to be within the scope of the present invention. Referring now to FIG. 3, the cable 90 and its connections to the housing member 12 and the printed circuit board 30 can be seen in greater detail. The cable 90 is comprised of an outer sheath material which encases a plurality of bundles 92

A-D within the cable 90. Each of these bundles 92 include a group of several individual wires, preferably sixteen wires, which are encased by an outer sheath material. The cable 90 and the bundles 92 enter the housing member 12 through a conduit opening 40 at the rear of the housing member. The bundles 92 are separated and mounted to the printed circuit board 30. The bundles 92 and cable 90 are secured in position by fasteners which are known in the art such as clips or Tie-Wraps® fasteners, although no limitation is intended. The individual wires 96 of each bundle 92 enter into the printed circuit board 30 through individual holes 97. The individual wires are then in electrical connection with the printed circuit board trace wires 98 which are in electrical contact with individual contact pins 32. A shielding device 100 is present for each individual bundle 92. The shielding devices 100 A-D are connected together and to the appropriate contact pin 32.

In this manner, the electrical signal which is received from the flexible circuit 16 and transferred to the contact pin 32 can be brought by electrical connections across the PC board 30 and into the individual wires 96 of the bundles 92 of the cable 90. The electrical signal is then transferred through the cable 90 to the medical instrument 130 (see FIG. 1) so that the patient's biological signs may be displayed or read by a medical professional.

The cable 90 provides many advantages by having groups of wires bundled together which are shielded as subcables or groups of subcables. With each wire bundle 92 A-D having an intermediate sheath of a flexible polymer material, movement relative to and between each group of cable is allowed within the larger outer cable 90 and its flexible polymer or rubber type sheath material. This combination provides signal integrity since each wire is shielded from external power line noise and flexibility as each bundle or group 92 A-D are allowed to slip over the other groups within the cable 90. Additionally, this design is more economical since the bundles or groups 92 A-D are much more affordable than individual miniature coaxial cable collectively, and are terminated much more easily since each individual shield need not be stripped of insulation and the braid then stripped back to expose a center conductor.

Figure 4:
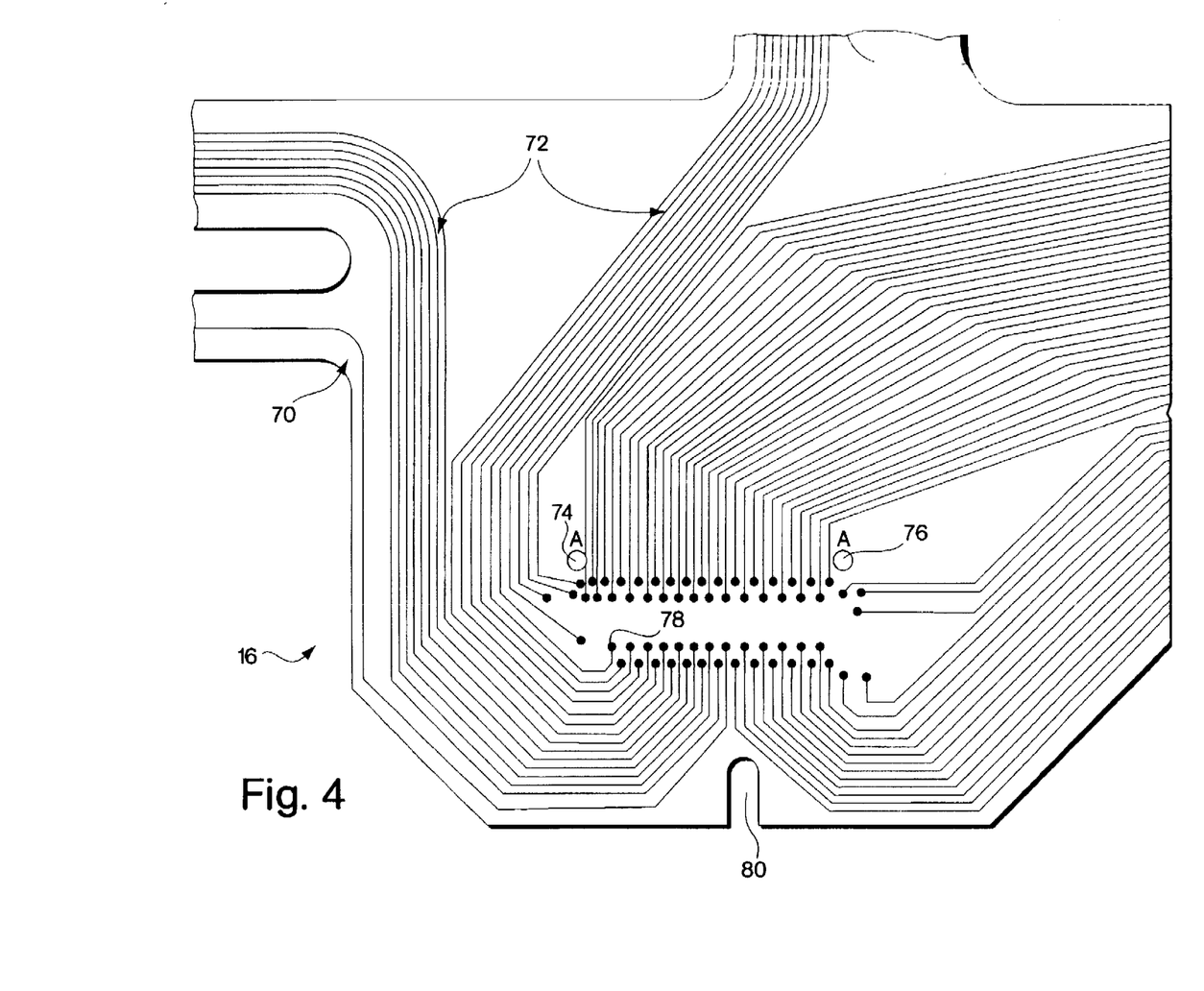
FIG. 4 is a planar view of a flexible electric circuit.

Referring now to FIG. 4, there is shown an embodiment of the flexible electric circuit 16 for use in the present invention. The flexible circuit 16 comprises a plurality of circuits or wires 72 encased in a flexible material 70. The circuits and wires extend to electrodes (See FIGS. 1 and 5) which are placed on the patient's body to receive biological signals at the first end of the wire and terminate at the opposite end of the wires in a series of conductive pads 78. The flexible circuit 16 may include one or more holes, 74 and 76, which are used to position the flexible circuit 16 onto the device 10 of the present invention.

In use of the device 10, the flexible electric circuit 16 can be positioned onto the device 10 so that the alignment apparatus 34 of the device 10 can protrude through the hole or holes of the flexible circuit member 16. The holes 74 and 76 of the flexible circuit 16 are positioned so that the conductive pads 78 would contact the electric connection points 32 of the device 10. A slot 80 may be used to cooperate in aligning the flexible circuit 16 with a tab or pin on the device 10. The upper member 14 of the device 10 can be raised by the user while inserting and aligning the flexible electric circuit 16 onto the contact points 32 and the alignment device 34. Once the flexible circuit is in place, the user may release the upper member 14 and the bias device of the device 10 will then return the upper member 14 to its lower or first position. In this manner, the clamp 48 would provide sufficient force over the electrical conductive pads 78 of the flexible circuit 16 to maintain strong electric contact between the pads 78 and the electric contact points 32 of the device 10. Once the flexible electric circuit 16 is clamped in place, the electrodes (See FIGS. 1 and 5) of the circuit 16 may be attached to the patient so that proper biological and electrical readings may be taken with the medical instrumentation. After all the desired readings have been made with the medical instrumentation, the flexible circuit 16 can be removed from the device by raising the upper member 14 to the raised or second position and removing the flexible circuit 16 from the alignment device 34. The connector device 10 of the present invention can therefore survive numerous connect/disconnect cycles in the health care or other environment.

The dimensions of the total electrical connection and clamping device 10 of the present invention in a preferred embodiment should be small enough to hold in one hand of a human being. Approximate dimensions for the device would be 2¾ inches wide by 3¼ inches long and 2 inches tall. The electrical contact means 32 would comprise rows of electrical connector pins. The connector pins would preferably be brass with at least 10 microns of gold plating on the tip of the pins to avoid contact electrical noise. Silver or other conductive materials may also be used.

Figure 5:
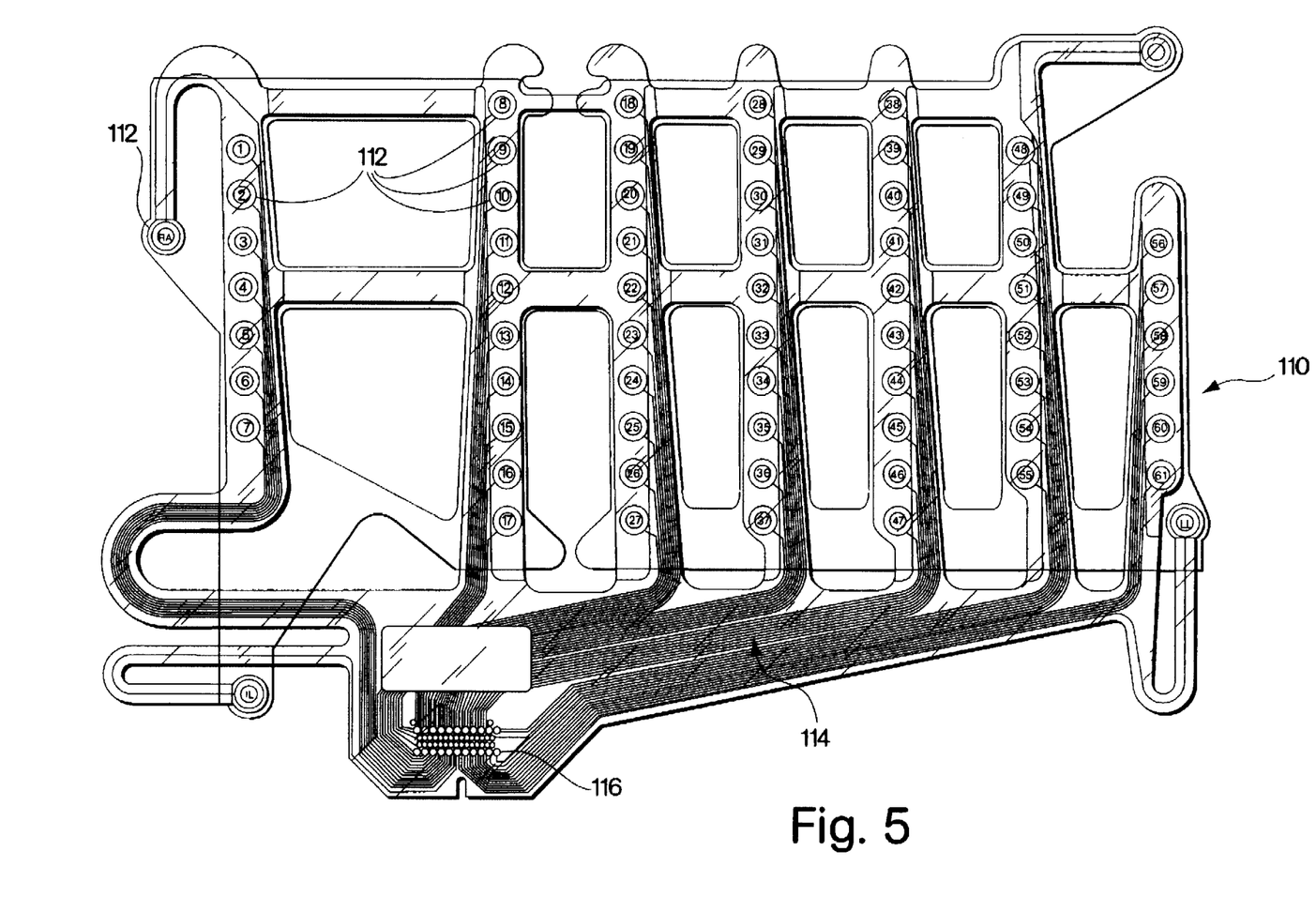
FIG. 5 is a top view of a flexible electrical medical harness which may be used with the present invention.

Although the embodiments of this invention are described with use of a flexible electric circuit, it should be appreciated that the device 10 can be used for anything which requires multiple uses and multiple electric connections. This may include, but is not limited to disposable blood pressure monitors, temperature monitors, pH sensors, cranial sensors, instruments which require attaching power to some device, or any other apparatus where an electrical signal may need to be routed from point A to point B. FIG. 5 provides an example of a multielectrode medical harness which may be used with the present invention. The harness 110 is a flexible film device with a plurality of electrodes 112 extending from a plurality of circuits 114. The electrodes 112 can be attached by adhesive or other known means to a patient at various points on the patient's body in order to receive various biological signals. These signals are transmitted electronically through the plurality of circuits 114 which terminate with contact points 116. In use with the present invention, these contact points 116 are positioned on the contact points 32 of the device 10 and clamping device 48 ensures sufficient electrical contact between the corresponding sets of contact points 116 and 32. Other types of sensors may function in similar manner, but no limitation is intended.

In a preferred embodiment, one of the holes 74 is oblong or elliptical in shape and has a major and a minor axis, and a second hole 76 is circular in shape. In the most preferred embodiment, the major axis of the oblong hole 74 is substantially parallel along line A—A with the circular hole 76. A slot 80 is also positioned at the edge of the flexible circuit 16.

In the preferred embodiment of the present invention, the circular hole 76 in the flex circuit 16 is mated to a corresponding alignment pin or fastener on the connector device. A second pin on the connector device 10 mates with the oblong hole 74 of the flex circuit 16 with precise dimensions in the minor axis of the oblong hole 74. The major axis of the oblong hole is substantially parallel with the line between these holes 74 and 76. The precise dimensions on the minor axis allow the position of the flexible circuit to be fixed relative to the circular hole 76 and corresponding alignment pin, thus aligning the connection points 78 on the flexible circuit 16 accurately relative to the connector device 10 and the electric contact points 32 of the device 10. The major axis dimension of the oblong hole 74 provides mechanical relief so that the flexible circuit 16 will remain flat on the connector device 10 when in use.

To further understand the function of the oblong hole 74 in the preferred embodiment, it should be appreciated that the two alignment pins 34A and 34B would be in a fixed relationship on the device 10. If these pair of pins are too close to each other relative to the flexible circuit holes 74 and 76 with which they mate, a ripple or wave in the flexible circuit 16 would be created when attempting to place the flexible circuit 16 on the alignment device 34. A ripple or wave in the flexible circuit 16 would be difficult to remove when the clamping device 48 is placed on to the electric contact pads 78 of the flexible circuit 16 and would prevent proper electric contact.

The minor axis of the oblong hole 74 has a dimension which is slightly larger than the diameter of the alignment pin 34. This dimension therefore allows the flexible circuit 16 to be placed over the pin 34 with a minor axis of the hole 74 mating with the alignment device 34. The dimension of the major axis of the oblong hole 74 should be long enough to account for the maximum manufacturing tolerances of the flexible circuit 16 and the connectors. In the preferred embodiment it is desired for the major axis to have a dimension which is at least equal to the sum of the diameter of the circular hole 76 plus twice the sum of the maximum tolerance of the spacing between the centers of the alignment holes 74 and 76 of the flexible circuit 16, and the maximum tolerance of the distance between respective centers of alignment pins 34A and 34B of the connector device 10. This dimension ensures that the flexible circuit 16 will lie flat on the connector device 10 when mated with the alignment device 34 and thereby provide sufficient electrical contact when the clamp holds the contacting pads 78 in position with the electric contact points 32.

In the preferred embodiment, the flexible circuit 16 also has a slot 80 along the edge or periphery while the connecting device 10 has a corresponding tab feature 55 (FIG. 2). This slot 80 allows the user to easily identify the proper attachment orientation for the flexible circuit 16. In this manner, the slot 80 and tab 55 are purposefully not centered so that the connector 10 will not mate with the flexible circuit 16 in an inverted position. Additionally, the flexible circuit electrical traces are located and positioned to prevent damage from the precision alignment means 34 in the case of accidental inverted attachment of the flexible circuit 16.

Preferably, the connector device 10 can be used with the flexible circuit 16 so that the circuit 16 may be attached and removed using a single hand operation. This is a result of the alignment features described above and the bias means which may be spring-loaded, along with the use of tapered tip precision alignment pins which easily seat into corresponding holes on the flexible circuit 16.

In the preferred embodiment, the electrical contacts 32 in the connector device 10 are raised buttons, but many shapes may be used including but not limited to circles, squares, bumps, pins, etc. These buttons contact the mating and corresponding conductive pads 78 on the flexible circuit harness 16. Low resistance contacts of less than 0.125 ohms can be obtained with as little as 10 grams of force per contact. Additionally, by raising the force to around 500 grams per contact changes the contact resistance by only about 0.025 ohms. These results indicate that an electrical connection of the present device 10 remains stable over a wide range of mechanical environmental conditions.

These electrical connections are facilitated by backing the flexible circuit 16 up with an elastomeric pad 48 as the clamping device. This pad provides the force required together with the upper member 14 and bias device 25 to press the flexible circuit and the conductive pads 78 into contact with the raised buttons 32. In this way, each pad 78 is given sufficient force to provide a reliable electrical connection. The elastomeric pad 48 also provides enough compliance to relax the flatness requirement of the flexible circuit 16 and thereby allow the flexible circuit 16 to be manufactured by a screening process rather than solely an etching process.

In the preferred embodiment of the present invention, the device 10 comprises a high density of electrical connections. This feature of the device 10 accounts for the fact that it is preferable for the device 10 to be small in size. The particular design of the present invention 10, in the preferred embodiment, therefore, provides for a large number of electrical interconnections in a very small area. In this implementation, there were 65 electrical connections made in an area. This density of electrical connections is possible because the elastomeric pad 48 provides pressure to each contact regardless of its location.

Another feature which should be noted in the preferred embodiment of the present invention is that the design of the electrical connector and clamping device is splash proof and resistant to the ingress of a variety of fluids which are used to clean the cable. This feature is desirable in a emergency room or medical situation where numerous fluids surround the electrical connecting device which may damage the circuits and connections which are contained within the device 10.

The device was tested for electrical contact resistance between two contacts and a flexible circuit contact strip. Experiments were performed with the electric contacts subjected to a free weight force of varying amounts. The electrical resistance of the contacts was then obtained using an ohmmeter. Test results for the two contact, four wire system are displayed on the chart below.

| FREE WEIGHT FORCE (grams) | #1 CONTACT STRIP (ohms) | #2 CONTACT STRIP (ohms) |
| --- | --- | --- |
| 10 | 0.247 | 0.128 |
| 110 | 0.213 | 0.115 |
| 210 | 0.210 | 0.108 |
| 10 | 0.250 | 0.134 |
| 30 | 0.241 | 0.126 |
| 40 | 0.239 | 0.122 |
| 20 | 0.240 | 0.131 |
| 60 | 0.228 | 0.121 |
| 10 | 0.249 | 0.132 |
| 110 | 0.222 | 0.117 |
| 510 | 0.210 | 0.105 |
| 10 | 0.245 | 0.138 |
| 310 | 0.214 | 0.105 |
| 410 | 0.212 | 0.105 |
| 10 | 0.245 | 0.137 |

*The chart displays contact resistance multiplied by 2 for each strip, therefore for a single contact point, the results above would be halved.

The offset voltage was −1.4 μV and remained steady. The contacts were turned around on a different strip and the offset voltage was then read as −2.2 μV, and remained steady. There was approximately 73 μV AC noise from the environment. At 5 grams per contact and with 65 contacts on the device, this gives 325 grams of weight which is approximately equal to 0.715 lbf for the entire contactors. Several strips were tried and in no case did the two contact, four wire resistances exceed 0.4 ohms, and averaged 0.2 ohms.

The cable shielding effectiveness was also tested. A sample of the microphone wire commonly used for shielding signals and a sample of the shielded sixteen-wire conduction were each mounted in a shielded, coaxial termination boxes with 17 centimeters of wire extending from the box. Each sample was mounted directly onto an oscilloscope channel using a barrel connector. The continuity and capacitance were checked. The microphone cord gave a value of 150 pF, in an open state. The sixteen-wire conductors gave a value of 50 pF in the open state.

The 60 Hz noise was measured at peak to peak values and found to be 44 mV for the microphone cord and less than 0.2 mV for the 16 wire conductors. This represents at least a 47 db (decibel) in screening, which reduces the cable noise to an insignificant level compared with any noise picked up from the electrical harness itself.

The cords were allowed to fold 180° and the force on the end was measured for each type of cord. Results show that for the microphone cord a force of 1 gram was measured and for the sixteen-wire conductor the force was measured as 6.5 grams for the entire wire or 0.4 grams per conductor.

These results show that the sixteen-wire conductor is much more supple with the values indicating that on a conservative estimate the sixteen-wire conductor is at least 2.5 times more supple.

Further embodiments of the above described invention may be appreciated by one of ordinary skill in the art and all such embodiments are considered to be within the scope of the present invention which is defined by the following claims.

What is claimed is:

1. An apparatus comprising, a housing member, an upper member and a printed circuit board, said housing member having a first surface with at least one electrical contact point, an alignment device, and a bias device, said first surface having a first end with a plurality of contact holes;

said upper member having first and second ends, with said first end having a clamping device and said second end pivotally connected to said bias device of said housing member;

said alignment device positioned to receive and said at least one electrical contact point positioned to electrically connect to an electric circuit which is secured by said clamping device, said printed circuit board having a plurality of contact pins positioned on said printed circuit board, said printed circuit board positioned beneath said housing member so that said plurality of contact pins protrude through said plurality of contact holes of said first surface of said housing member to form said at least one electrical contact point.

2. The apparatus of claim 1, wherein said alignment device comprises at least one alignment pin on said first surface of said housing member.

3. The apparatus of claim 1 wherein said upper member further comprises a cover piece located at said second end of said upper member.

4. The apparatus of claim 3, wherein said bias device comprises a pivot bar and at least one spring, said pivot bar having a pivot axis with a pivot point, said at least one spring and said pivot bar cooperating with said cover piece of said upper member to pivotally connect said upper member to said housing member.

5. An apparatus comprising, a housing member and an upper member;

said housing member having a first surface with a plurality of holes and a bias device;

said upper member having first and second ends, said first end having a clamping device and said second end connected to said bias device of said housing member;

an alignment device protruding through at least one of said plurality of holes of said first surface of said housing member to receive an electric circuit;

at least one electrical contact point protruding through at least one of said plurality of holes of said first surface of said housing member.

6. The apparatus of claim 5, wherein said upper member further comprises a cover piece located at said second end.

7. The apparatus of claim 5 wherein said bias device comprises a pivot bar and at least one spring, said pivot bar having a pivot axis with a pivot point, said at least one spring and said pivot bar cooperating with said cover piece of said upper member to pivotally connect said upper member to said housing member.

8. The apparatus of claim 5 wherein said upper member has a first position and a second position, wherein said first position of said upper member clamps said electric circuit to said at least one electrical contact point, and said second position raises said clamping device to allow removal of said electric circuit.

9. The apparatus of claim 8 wherein said upper member is returned to said first position from said second position by said bias device.

* * * * *

UNITED STATES PATENT AND TRADEMARK OFFICE
CERTIFICATE OF CORRECTION

PATENT NO. : 5,733151
DATED : March 31, 1998
INVENTOR(S) : David Edsall, et al.

Page 1 of 2

It is certified that error appears in the above-identified patent and that said Letters Patent is hereby corrected as shown below:

In the Drawings:

Delete Drawing Sheet 3, and substitute therefor the Drawing Sheet, consisting of Figure 3, as shown on the attached page Signed and Sealed this First Day of September, 1998

*Attest:*

BRUCE LEHMAN

*Attesting Officer*     *Commissioner of Patents and Trademarks*

Fig. 3